(12) United States Patent
Lerman et al.

(10) Patent No.: US 6,572,587 B2
(45) Date of Patent: Jun. 3, 2003

(54) ANCHORING DEVICE FOR MEDICAL APPARATUS

(76) Inventors: Benjamin S. Lerman, 1828 Hopkins St., Berkeley, CA (US) 94707; George Khait, 612 Westline Dr., Alameda, CA (US) 94501; Robb Moore, 1410 Ebener St., Redwood City, CA (US) 94059

( * ) Notice: Subject to any disclaimer, the term of this patent is extended or adjusted under 35 U.S.C. 154(b) by 0 days.

(21) Appl. No.: 09/756,977

(22) Filed: Jan. 9, 2001

(65) Prior Publication Data

US 2001/0056261 A1 Dec. 27, 2001

Related U.S. Application Data

(60) Provisional application No. 60/175,297, filed on Jan. 10, 2000.

(51) Int. Cl.⁷ ............................ A61M 5/32; A61B 17/08; A61D 1/00
(52) U.S. Cl. ...................... 604/174; 604/175; 604/178; 606/213; 606/216
(58) Field of Search ................................ 606/213, 216; 604/174–178; A61M 5/32

(56) References Cited

U.S. PATENT DOCUMENTS

| | | | |
|---|---|---|---|
| 3,825,010 A | | 7/1974 | McDonald |
| 4,164,943 A | * | 8/1979 | Hill et al. .................... 128/348 |
| 4,345,601 A | | 8/1982 | Fukuda |
| 4,392,853 A | * | 7/1983 | Muto ......................... 604/171 |
| 4,397,647 A | | 8/1983 | Gordon |
| 4,683,895 A | | 8/1987 | Pohndorf |
| 4,781,692 A | * | 11/1988 | Jagger et al. ................ 604/164 |
| 4,798,595 A | | 1/1989 | Andersson et al. |
| 4,906,233 A | | 3/1990 | Moriuchi et al. |
| 5,002,563 A | | 3/1991 | Pyka et al. |
| 5,105,807 A | | 4/1992 | Kahn et al. |
| 5,263,939 A | | 11/1993 | Wortrich |
| 5,540,648 A | * | 7/1996 | Yoon ........................... 600/114 |
| 5,730,758 A | | 3/1998 | Allgeyer |
| 5,792,115 A | | 8/1998 | Horn |
| 5,810,882 A | | 9/1998 | Bolduc et al. |
| 5,814,021 A | | 9/1998 | Balbierz |
| 5,833,667 A | | 11/1998 | Bierman |
| 5,855,591 A | | 1/1999 | Bierman |
| 6,231,581 B1 | * | 5/2001 | Shank et al. ................ 606/157 |
| 6,355,014 B1 | * | 3/2002 | Zadno-Azizi et al. ..... 604/99.02 |
| 6,361,523 B1 | * | 3/2002 | Bierman ..................... 604/174 |

* cited by examiner

*Primary Examiner*—Kevin Shaver
*Assistant Examiner*—Anuradha Ramana
(74) *Attorney, Agent, or Firm*—Vierra Magen Marcus Harmon & DeNiro LLP

(57) ABSTRACT

A system for anchoring a catheter to the body of an individual is disclosed, which includes a device-grasping mechanism and an anchoring mechanism. The device-grasping mechanism a housing in which a catheter or other medical device can be securely and rapidly attached or detached from the anchoring mechanism. The anchoring mechanism includes one or more arcuate needles attached to each other by means of a shaft. The arcuate needles are rotatably supported on the housing, and are locked into position when in the engaged and unengaged positions. The anchoring mechanism further includes portions in which the sharpened tips of the arcuate needles reside when in the engaged and unengaged positions in order to prevent injury to medical or other personnel.

24 Claims, 13 Drawing Sheets

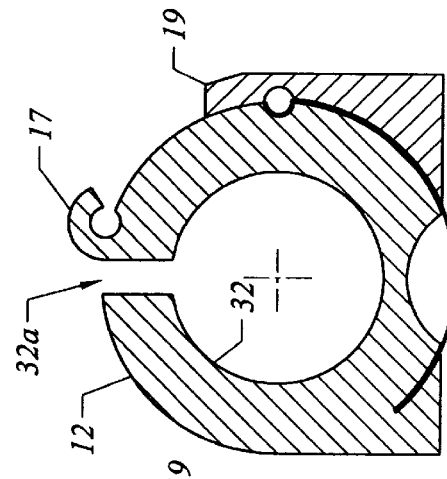
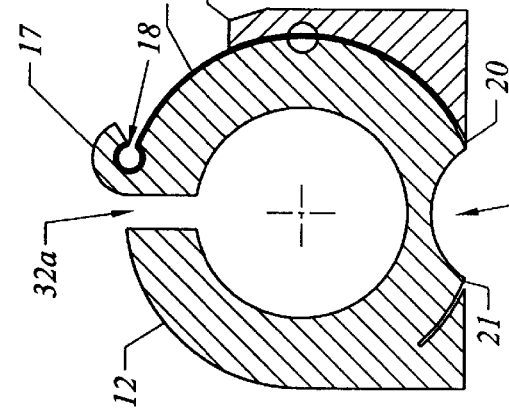
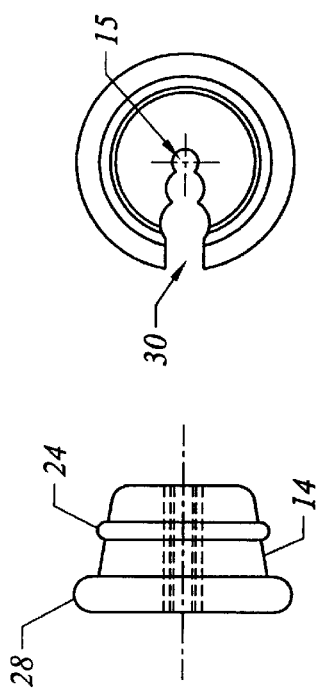
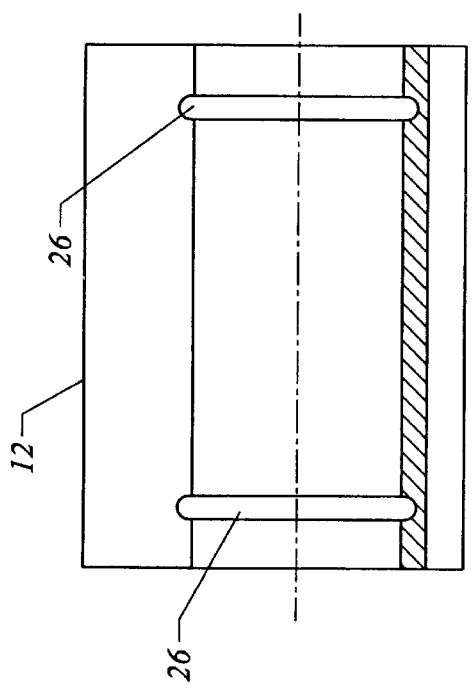

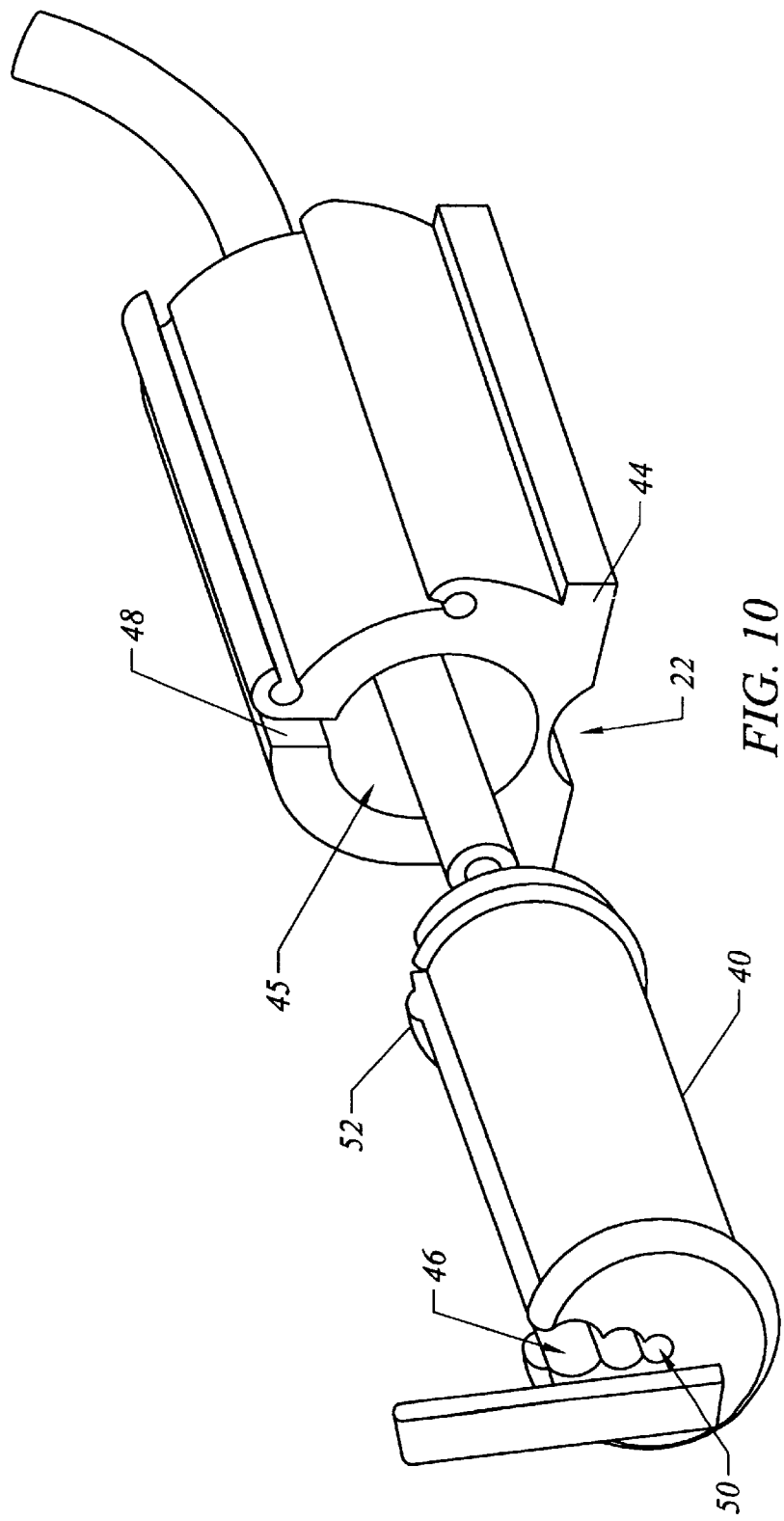

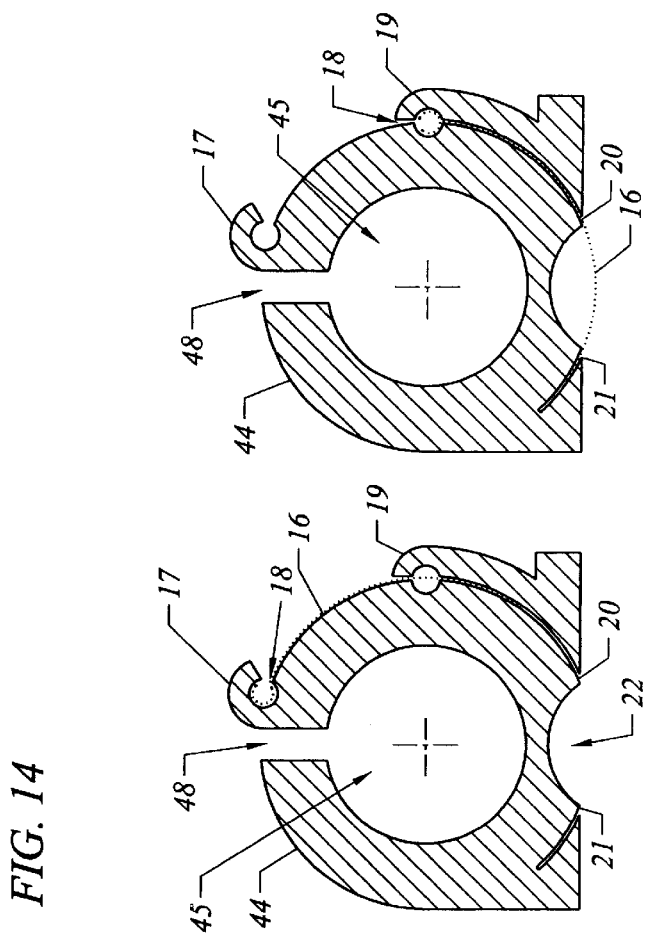
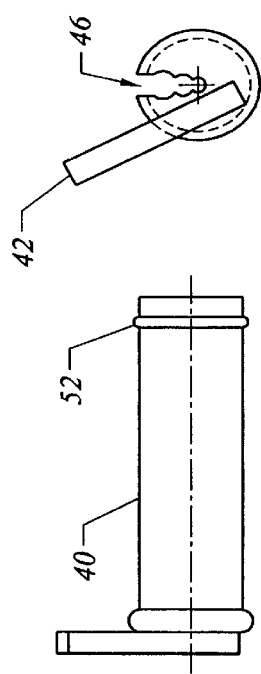
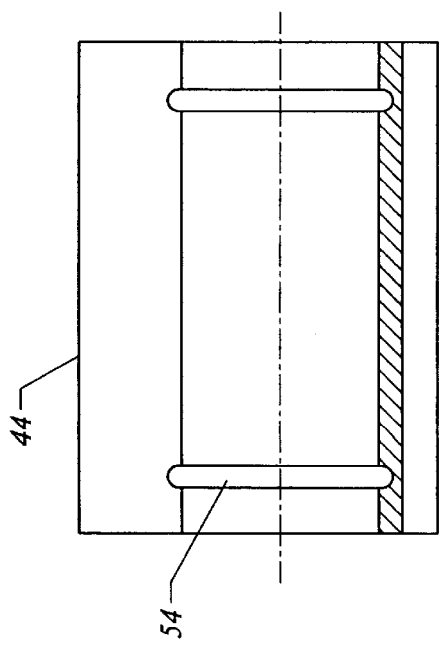
FIG. 11
FIG. 12
FIG. 13
FIG. 14
FIG. 15

ANCHORING DEVICE FOR MEDICAL APPARATUS

CROSS-REFERENCE TO RELATED APPLICATIONS

This application claims priority from Provisional Application Serial No. 60/175,297, filed on Jan. 10, 2000.

BACKGROUND OF THE INVENTION

1. Field of the Invention

This invention relates to medical devices, and more particularly to medical devices for securing surgical catheters and the like to a patient's skin or tissue to prevent dislodgment.

2. Description of the Prior Art

A variety of apparatus used in human and veterinary medicine must be securely attached to a patient, either internally or to the skin. The methods employed for this vary, but excessive time-consumption, unreliability, expense, and risk of injury mar each of them. An apparatus commonly requiring a secure attachment is a catheter. Catheters (tubes, usually composed of plastic) are commonly inserted into blood vessels to administer fluids, medications, or nutrients, to withdraw blood, to measure pressures within the blood vessel or to allow the passage of various instruments through the vessel (such as a pacemaker wire). Catheters may be inserted into a variety of body cavities as well, such as the chest or abdomen. When a simple catheter is inserted into a small peripheral vein (an ordinary intravenous or "I.V."), it is generally secured with adhesive tape to the patient's skin adjacent the point of insertion. But most other surgical catheters (i.e. those inserted into arteries, major veins, or body cavities, such as the chest or abdomen) must be more reliably secured. Accidental migration to an undesired location or dislodgment of such a catheter can cause bleeding, infection, collapse of a lung, heart rhythm abnormalities, and other potentially fatal complications. Even if no such complication ensues, such accidental migration or dislodgment requires repositioning or replacing the catheter which wastes time and materials and subjects the patient to further risks and additional trauma and punctures.

Several methods have been used to attempt to secure surgical catheters more reliably. Most commonly, a pair of plastic wings, each having an eyelet, are incorporated into the hub of the catheter. The catheter is inserted into the patient, up to the hub. The operator then passes a needle and thread through one of the eyelets, then through the patient's skin, then ties a knot, cuts the thread and repeats the process on the opposite eyelet.

In some cases the catheter is not designed to be inserted all the way to the hub. Instead it must be inserted to a particular depth determined by the anatomy of a particular patient. In these instances (or in the case of catheters, such as chest tubes, which have no hub) the thread must be cinched tightly around the catheter and sewn through the skin. Alternatively, a catheter-grasping device may be attached anywhere along the length of the catheter. Currently a popular catheter-grasping device consists of two concentric plastic collars, each with a pair of protruding wings, each of which has an eyelet. The inner collar is of pliable plastic and the outer collar is of rigid plastic. After inserting the catheter to the desired depth, the operator slips the inner collar over the protruding portion of the catheter, adjacent the skin. The operator then snaps the outer collar over the inner collar, and then sews the entire assembly in place as described above.

This sewing technique is not entirely reliable-sutures often break, especially if tension must be applied to cinch the catheter. The pressure exerted on the skin both by the sutures and by the apparatus it is securing are highly variable and operator dependent. Too little pressure may result in a loose, floppy attachment which allows the catheter to slide in and out of its insertion site, with the dangerous consequence of introducing germs from the patient's skin into the bloodstream. Too much pressure may cause skin necrosis and breakdown, which may cause a persistent ulcer, infections, and/or the dislodgment of the catheter.

Moreover, sewing is also tedious and time-consuming, particularly when a catheter grasping device is applied. Many small loose parts must be fumbled with (the needle and thread, and the two parts of the catheter-grasping device), multiplying the chances that one of these parts will be dropped off the sterile field and contaminated. Straight needles are generally provided for this purpose because they eliminate the cost of a curved needle and the instrument to hold it (a needle driver), but as a result the skin must be awkwardly pinched, and the suturing process itself is more traumatic. There is also a risk of penetrating too deeply with the needle, and puncturing a vital structure, or even the catheter itself. These problems occur when attempting to attach this type of catheter-grasping device to a patient who is motionless. When the patient is unable or unwilling to remain motionless long enough for the catheter-grasping device to be attached, this procedure becomes even more difficult and prone to error.

After a catheter has been secured, its position is verified with an x-ray (radiograph). If, as often happens, the catheter is found to be in the wrong position, the time wasted is multiplied, as it is then necessary to undo all the above steps and repeat them. Because catheters of this type are often inserted in emergency situations, time is of the essence. An operator wasting time securing a catheter cannot attend to other pressing matters, and may physically interfere with the access of other health-care personnel to the patient.

But the greatest drawback of sewing a catheter in place is the risk of inadvertent needle-stick injury, a risk which is magnified by the degree to which the operator is rushing to complete an emergency procedure. This risk is also magnified by the straight needle provided by almost every kit manufacturer to save the additional cost of a curved needle and needle-driver. Straight needles require more handling by the operator, and they force the operator to place his/her non-dominant hand in harm's way because the operator must pinch up the skin to pass the needle through it. Moreover, every needle used in a medical procedure jeopardizes many people besides the operator-nurses, technicians, custodians, and whoever might come into contact with the needle. In recognition of the risk of lethal, incurable blood-borne diseases such as HIV and Hepatitis C, the recently approved federal Needlestick Safety and Prevention Act mandates the use of safer alternatives to conventional needles wherever possible.

Adhesive-backed platforms (for example, U.S. Pat. Nos. 5,855,591 and 5,833,667 to Bierman) have also been proposed as catheter securing devices, but, for lack of reliability, have not found wide acceptance. The manufacturer's warning with one such device reads as follows: "Catheter should be sutured to the skin in situations where loss of adherence may occur such as: confused patient, unattended central vascular device, extreme diaphoresis or denuded skin." These conditions are very common. For example, even the sickest patients must occasionally be left unattended for short periods. Thus adhesives are unacceptable, even by the standards of their manufacturer, for catheters in which a high degree of security is required. But even if the reliability of adhesives were not in doubt, they suffer from other serious drawbacks. They cannot be used on patients who are very sweaty or have very thin, fragile skin. Yet patients who require a catheter in a major vessel are generally the most ill-a disproportionately large number of them will be very sweaty. Patients who are elderly and/or have chronic illnesses are also among those most likely to need such a catheter. Yet they often have paper-thin skin which will be torn off when the time comes to remove an adhesive. Various solvents are recommended to help remove the adhesive, but these are harsh materials that may themselves damage fragile skin, even if a nurse is patient enough to carry out the tedious and lengthy process of applying them with a cotton-tipped applicator beneath the leading edge of the platform as it is peeled back bit by bit from the skin.

Various straps have been proposed to secure a catheter to a limb, generally involving the use of hook-and-loop closures. None of these has found wide use, even for peripheral venous catheters which do not require a high degree of security. They have no application for central venous catheters which do require a high degree of security, and which, moreover, must generally be affixed to portions of the body which are not conveniently encircled by a strap.

U.S. Pat. No. 5,730,758 to Allgeyer describes a staple and staple applicator for use in skin fixation of catheters, designed to replace the suture placed through the eyelets of existing catheter-grasping devices or hubs. This device requires cumbersome additional equipment (the staple applicator and a staple remover), which is unnecessarily complex because it requires the use of a deforming staple. To allow the use of a stapler without an anvil, the operator must manually pinch the skin so that a fold of skin protrudes up between the opposing points of the staple. The fold of skin so pinched must be precisely located at the proper distance from the eyelet, and neither too wide to fit between the opposing points of the staple, nor too narrow to give adequate purchase for the staple. (Alternatively, to avoid the need for pinching the skin, a still more complex stapler with an anvil would be needed, which Allgeyer does not teach.) The operator must simultaneously carefully align the staple points with the eyelets and the fold of skin. The depth of the staple bite achieved is unpredictable, so that a tenuous attachment may result. If a radiograph subsequently determines that the catheter position must be adjusted, the staples must be removed and discarded, and the patient's skin must be pierced again with new staples after the adjustment has been made. As with the suturing method discussed above, when the patient is unable or unwilling to remain motionless, the device taught by Allgeyer is even more difficult to use.

Nearly all surgical staples require either that the staple be deformed to apply it, or that a retaining piece be used to receive and hold the barbed end of the staple point. U.S. Pat. No. 5,810,882 to Bolduc et al. reveals a surgical helical fastener which requires neither a means to deform the staple, nor a retaining piece. However, Bolduc teaches the use of the device only within a patient's body; and more particularly for the purpose of repairing a hernia. Moreover, Bolduc does not teach the use of the device as an integral part of an apparatus-securing device.

Similarly, U.S. Pat. No. 5,540,648 to Yoon discloses an instrument stabilizer with anchoring system for use during endoscopic procedures, in which a number of individual needles are mounted in guides protruding up from the surface of a platform intended for application to an external surface of an anatomical cavity. However, Yoon teaches the use of this stabilizer only during endoscopic procedures, which are brief (a few hours at most), and take place in controlled conditions under anesthesia. The multiple individual needles must be deployed one at a time, which is unsuitably time consuming for application of vascular catheters and many other surgical catheters in which time is of the essence. Furthermore, no mechanism is disclosed for retaining the needles in a deployed position to prevent subsequent dislodgment. Likewise, the Yoon device is unsuitable for use with the many surgical catheters which must remain in place for days or weeks. Yoon further fails to disclose a mechanism to prevent the inadvertent redeployment of a needle after it has been withdrawn, thus creating the risk of contaminated needlestick injury. Yoon also teaches the attachment of an apparatus or cylindrical structure perpendicularly to the surface of the device, in contrast to the need for parallel attachment for most surgical catheters which need to remain in place for a significant length of time, and/or which enter a blood vessel. More importantly, the design of the two types of needles disclosed by Yoon (curved and helical) requires in each case a guide of some sort protruding up from the surface of the stabilizer. While this is suitable for endoscopic procedures in which other equipment will in any case be mounted perpendicular to the surface of the stabilizer, it is highly undesirable for the fixation of surgical apparatus such as vascular catheters, in which a low profile attachment is needed, both for patient comfort and to prevent inadvertent dislodgment of the apparatus.

U.S. Pat. No. 4,164,943 to Hill describes a catheter anchor that employs a number of helical needles protruding from its base. The device is rotated against the skin to screw these needles into the skin. Hill teaches no means for protecting the operator or other personnel from contaminated needlestick injury after the device is withdrawn. Hill further fails to provide a mechanism for preventing the device from rotating in a reverse direction and thus being dislodged inadvertently. If the helical needles employed attack the skin at a low angle, they are likely to lacerate rather than cleanly puncture the skin. Alternatively, if the needles attack at a very high angle, they will need to penetrate to a dangerous depth in order to achieve a secure attachment. The Hill catheter grasping mechanism is bulky, needlessly complex, and it protrudes from the skin to a degree that is undesirable for reasons noted above. It also results in the catheter being secured some height above the skin, whereas the ideal attachment occurs along the shaft of the catheter as close as possible to the point at which it penetrates the skin.

Andersson, et al, disclose in U.S. Pat. No. 4,798,595, an injection device designed to deliver medications to the subcutaneous tissues. Accordingly, Andersson does not involve the use of an anchoring device, and the single needle with which it is fitted does not produce a secure attachment. While Andersson does provide a low profile device after it is fully deployed, it does so only by means of an elaborate and bulky mechanism which must then be removed and discarded. Even if Andersson were to suggest the use of the disclosed device for anchoring functions, and it is submitted that there is no such suggestion, the device would be needlessly expensive and cumbersome. Moreover, no protection against needlestick injury would be provided.

It is an object of the present invention to provide a device for attaching an apparatus to the body which:

(a) can be secured without the use of a needle and with a vastly reduced risk of transmission of blood-borne diseases;

(b) can be secured instantly;

(c) is reliable and secure, with a predictable and optimal degree of pressure against the skin or tissue;

(d) is self-contained and does not require any additional equipment for application or removal;

(e) can be detached from the body instantly and without damage to the skin or tissue;

(f) can be detached from the skin or tissue and reattached in a new position without the use of new equipment;

(g) can be used on any patient regardless of their skin condition, mental state or need for constant monitoring;

(h) reliably and securely grasps a catheter;

(i) can be made to release the catheter for adjustment and then to grasp it again, without being detached from the skin or tissue;

(j) has no loose parts, thus minimizing the chance of dropping a part and thereby contaminating it; and (k) has a low profile and does not interfere with patient care or patient mobility, or cause undue discomfort to the patient.

It is also desirable to provide a device which is inexpensive to produce, which will work with a wide variety of catheters, and which can easily be employed to anchor other medical apparatus, besides catheters, to a patient's body.

BRIEF SUMMARY OF THE INVENTION

The present invention is a method and device for securing an apparatus to the body which operates quickly, reliably, and without risk of needle-stick injuries by use of an arcuate anchor, the point of which is pushed out of the device, through the skin or tissue, and back into the device, thus grasping a bite of tissue between the shaft of the anchor and the device.

Other objects and advantages of the present invention will become apparent from the following description of the preferred embodiments taken in conjunction with the accompanying drawings, wherein like parts in each of the several figures are identified by the same reference numbers.

BRIEF DESCRIPTION OF THE DRAWINGS

FIG. 2 is a cross-section view of the anchoring device shown in FIG. 1, showing an anchor in an unengaged position with respect to an anchor track.

FIG. 3 is a cross-section view of the anchoring device shown in FIG. 1, showing the anchor in an engaged position with respect to the anchor track.

FIG. 4 is a side view of a plug shown in FIG. 1.

FIG. 5 is a axial view of the plug shown in FIGS. 1 and 4, showing the configuration of the plug when engaged in the housing.

FIG. 6 is a longitudinal cross-section view of the housing shown in FIGS. 1, 2 and 3.

FIG. 10 is an exploded view of an eccentric catheter grasping device according to a third embodiment of the present invention.

FIG. 11 is a cross-section view of the eccentric housing shown in FIG. 10, showing the anchor in the unengaged position with respect to the anchor track.

FIG. 12 is cross section view of the eccentric housing shown in FIG. 10, showing the anchor in the engaged position with respect to the anchor track.

FIG. 13 is a side view of the eccentric rotatable core shown in FIG. 10.

FIG. 14 is an axial view of the eccentric rotatable core shown in FIGS. 10 and 13.

FIG. 15 is a longitudinal cross-section view of the eccentric housing shown in FIG. 10.

DETAILED DESCRIPTION OF THE INVENTION

Figure 1:
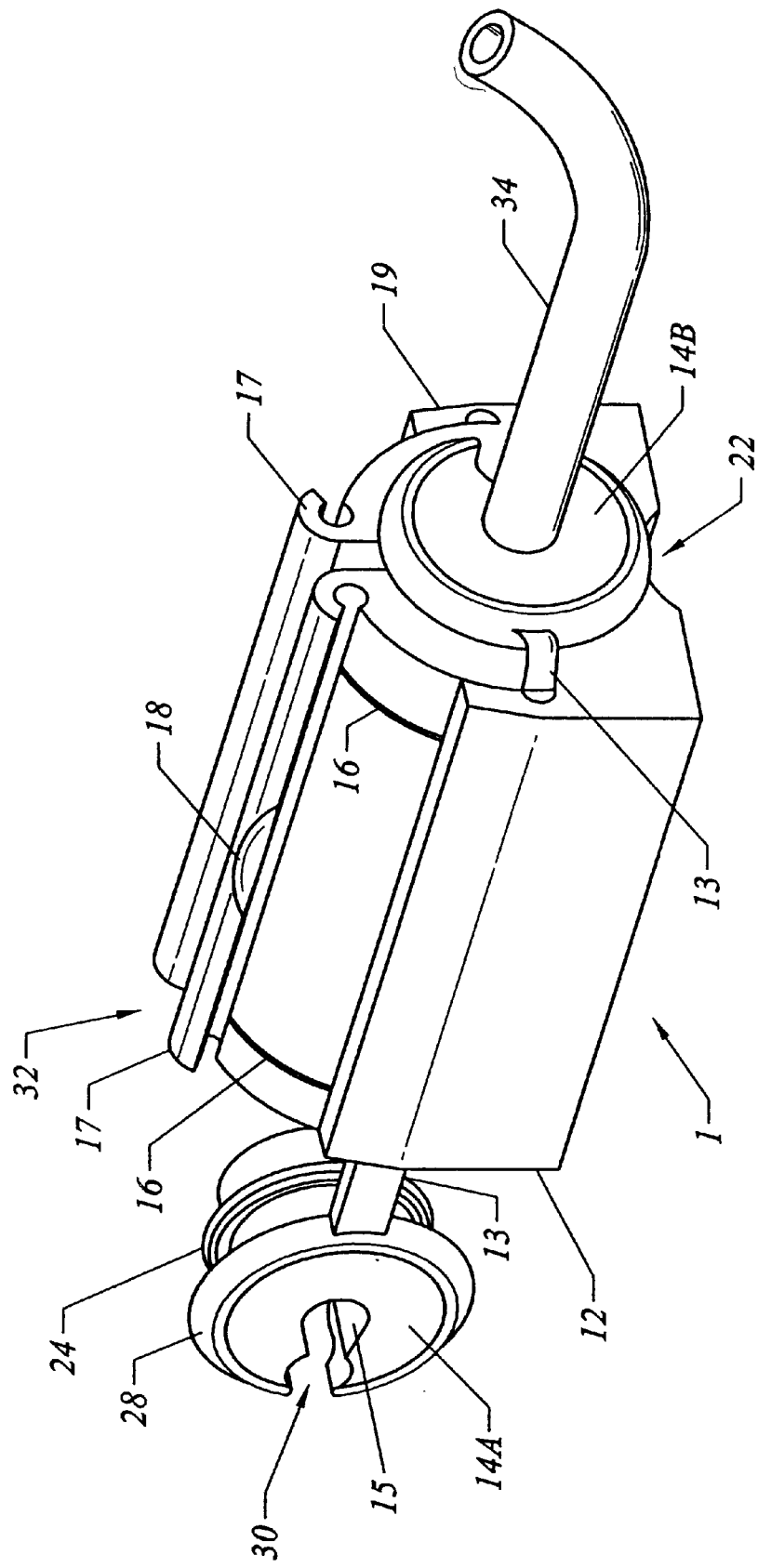
FIG. 1 shows a perspective view of an anchoring device according to a first embodiment of the present invention.

FIG. 1 is a perspective view of a catheter anchoring device 1 according to a first embodiment of the present invention. A catheter grasping means 2 includes two plugs 14a and 14b, and a housing 12. Plug 14b is shown fully engaged in housing 12, while plug 14a is shown in the open, disengaged position. Both plugs 14a and 14b are attached to housing 12 by means of a hinge 13. FIG. 1 also shows a catheter engaged with catheter anchoring device 1. The distal, or left, end of this catheter, not shown, is inserted through the skin and into a blood vessel of a patient.

Referring to FIGS. 1, 2 and 3, housing 12 includes a bore 32 which extends the length of housing 12, and a slit 32a that extends the length of the top of housing 12. Anchors 16 are disposed on housing 12, and are guided along an anchor track 20 formed in housing 12 (shown in FIG. 2). Anchor track 20 has an arc that is the same radius as that of anchor 16 and a plane that is perpendicular to the longitudinal axis of housing 12. Unengaged retaining lip 17 is disposed adjacent to slit 32a, and is an overhanging lip formed from a flexible material that serves to secure anchors 16 in the unengaged position. An engaged retaining lip 19, also formed from a flexible material, is disposed below unengaged retaining lip 17 and serves to secure anchors 16 in the engaged position. A groove 22 is formed in the bottom of housing 12, and is a semi-circular channel that extends the length thereof.

Anchors 16 are arcuate wire members formed from any material suitable for use in medical applications, such as metal, plastic, or the like, and each of a first end thereof are sharpened. Anchors 16 are connected together at a second end thereof by means of anchor drive bar 18. Anchor drive bar 18 has a gauge that is similar or larger than that of anchors 16, and as with anchors 16, anchor drive bar 18 can be formed from any material suitable for use in medical applications, such as metal, plastic, or the like. A handle means can also be disposed on or formed in the anchor drive bar 18, which allows the operator to grasp anchor drive bar 18 more easily. Anchors 16 are shown in the unengaged position in FIG. 1, with anchor drive bar 18 secured by unengaged retaining lip 17. FIG. 2 shows this configuration in cross section. FIG. 3 shows anchors 16 in the engaged position, and anchor drive bar 18 secured behind engaged retaining lip 19.

Plugs 14a and 14b are identical, and thus only one is shown in profile in FIG. 4. Plugs 14a and 14b are substantially frustum-shaped, and are formed from a semi-rigid, pliable material such as rubber. They each include a locking ridge 24, which is an annular ridge protruding from the circumference thereof near their narrow ends, and a flange 28, which is an annular ridge protruding from the circumference thereof at their wide ends. An end-on view of a plug 14 is shown in FIG. 5. Plugs 14a and 14b each further include plug slits 30 and bores 15. Each bore 15 extends axially through each plug 14a and 14b, and each plug slit 30 is disposed in the side of each plug 14a and 14b.

FIG. 6 is a longitudinal section through housing 12 showing locking grooves 26. These are circular grooves formed in the internal wall of housing 12 in bore 32, whose plane is perpendicular to the longitudinal axis of housing 12. The distance from each end of housing 12 to locking grooves 26 is approximately the same as the distance from the inside edge of each flange 28 to locking ridge 24 (as shown in FIG. 4). This groove/ridge combination locks plugs 14a and 14b in place when they have been inserted to the proper point into housing 12 (described further below).

In order to secure catheter 34 to a patient's skin, the operator must first fit it into bore 15 of either plug 14a or 14b (for the purpose of this example, plug 14a will be used). If the tip of catheter 34 has not yet been inserted into the patient, it can be slid axially through bore 32 of housing 12, or may be passed through housing slit 32a by parting the flexible walls of housing 12 and then into bore 32. After catheter 34 is properly placed in the patient's body, it is then inserted into bore 15 of plug 14a through plug slit 30 by parting the flexible walls thereof. Plug 14a can then be rotated on its hinge 13 and partially engaged with housing 12.

If the catheter tip has already been inserted into the patient, the proximal shaft of catheter 34 is passed through housing slit 32a by parting the flexible walls of housing 12 and then into bore 32. Plug 14a is then rotated on its hinge 13, and the shaft of catheter 34 is guided through plug slit 30 and into bore 15. Plug 14a can then be rotated on its hinge 13 and partially engaged with housing 12.

If the operator so desires, catheter 34 can be engaged with plug 14b in the same manner described above, or can choose to secure catheter 34 with only plug 14a.

The operator then pushes plug 14a into housing 12 until locking ridge 24 engages locking groove 26. If plug 14b is used, it is locked as well. By pushing plug 14a and/or 14b into housing 12, the diameter of bore 15 narrows and securely grasps catheter 34 in a manner that prevents axial movement thereof, but without unduly narrowing its diameter. (If topical anesthesia is needed, it is infiltrated at this time, into the area of skin where the device will be secured.)

After securing catheter 34 into the device as described above, the operator then presses the surface of the device containing groove 22 against the patient's skin with light pressure (not shown), which causes a ridge of skin (not shown) to be pushed up into groove 22. The operator then pulls anchor drive bar 18 over unengaged retaining lip 17 and then depresses anchor drive bar 18, which in turn drives anchors 16 through anchor tracks 20, through the patient's skin, and into anchor recess 21. (The depth of penetration of anchor 16 through the skin is predetermined by the gap between the apex of groove 22 and the nadir of anchors 16.) In its fully depressed position, anchor drive bar 18 locks beneath engaged retaining lip 19. This completes the operation of securing the catheter 34 to the device and the device to the skin.

If the catheter 34 must be advanced or withdrawn after this operation is complete (for example, if a radiograph demonstrates that the tip of catheter 34 is improperly positioned), the operator pulls on flange(s) 28 to partially withdraw plug 14a and/or 14b from housing 12. Catheter 34 will then slide easily through bore 15 to the desired new position, and then the operator pushes plug 14a and/or 14b back into the locked position in housing 12.

When the catheter is to be removed from the patient, the operator can easily detach the entire device from the patient's skin simply by reversing the procedure described above. The operator pulls anchor drive bar 18 from beneath engaged retaining lip 19. Then anchor drive bar 18 is lifted upward, which withdraws anchors 16 from the skin, and anchor drive bar 18 is locked beneath unengaged retaining lip 17. This keeps the points of anchors 16 locked within anchor track 20, so that no inadvertent skin puncture can occur. Catheter 34 can then be withdrawn from the patient with the anchoring device still attached to catheter 34, and the whole assembly can be discarded.

If for some reason the anchoring device needs to be repositioned on the patient's skin, while catheter 34 remains in place, anchors 16 can be withdrawn as described above. The device can then be moved, with catheter 34 still attached to it, to the desired location. If the new desired location is at a different distance from the skin insertion site of catheter 34, the operator follows the steps described above in order to reposition the device along the length of catheter 34. The device is then reapplied as described above.

Figure 9:
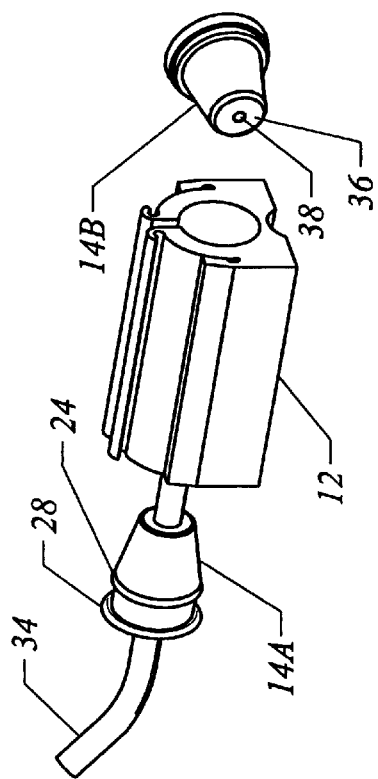
FIG. 9 is a perspective view of an anchoring device according to the second embodiment of the present invention.
Figure 8:
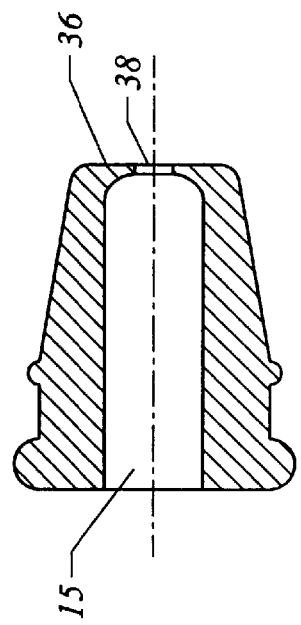
FIG. 8 is a longitudinal cross section view of the universal plug shown in FIG. 7.
Figure 7:
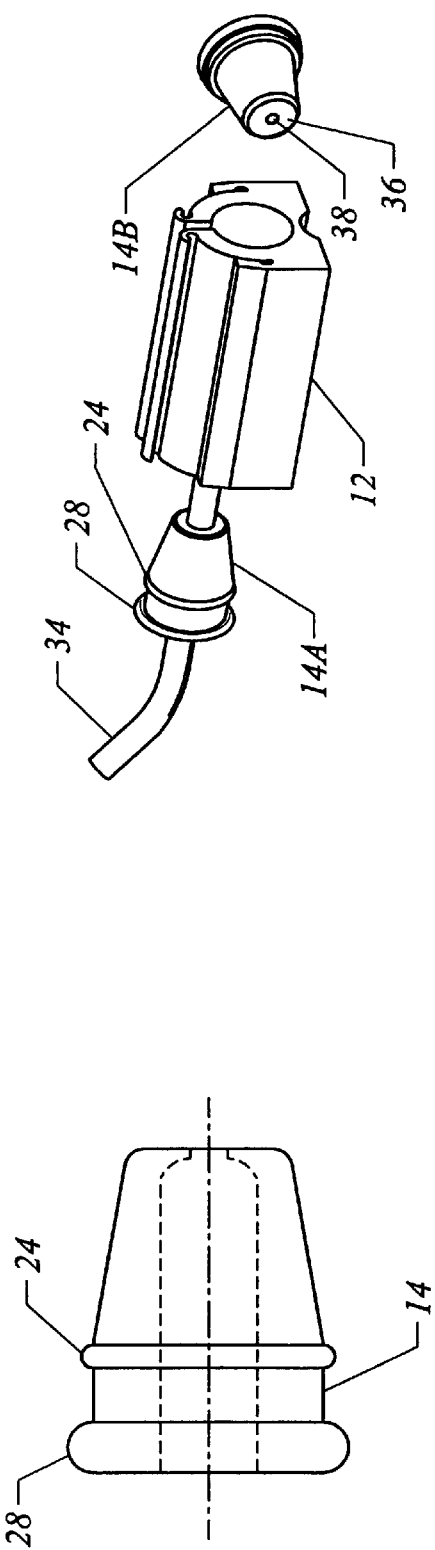
FIG. 7 is a side view of a universal plug according to a second embodiment of the present invention.

An alternative embodiment of plugs 14a and 14b is seen in profile in FIG. 7, showing flange 28 and locking ridge 24, identical to those seen in earlier figures. The longitudinal section in FIG. 8 demonstrates that bore 15 is wider in this embodiment, and that a diaphragm 36 is provided at the inserting end of plugs 14a and 14b. Diaphragm 36 is a disc of a rubbery material, tapering from thickest at its periphery to very thin near its center. It covers all but the central portion of bore 15, where a diaphragm hole 38 is provided. The perspective view of FIG. 9 shows diaphragm hole 38 present at the center of diaphragm 36 of plug 14b, through which catheter 34 has not yet been passed. At the far end of this figure, catheter 34 is shown after its tip has been passed through bore 15 and diaphragm hole 38 of plug 14b.

In this alternative embodiment, plugs 14a and 14b will secure not only a catheter 34 whose outer diameter is nearly that of bore 15, but will also secure catheters whose outer diameters range in size from that of diaphragm hole 38 at the smallest, and up to that of bore 15 at the largest. The operator pushes the tip of any catheter within that range of sizes through bore 15 (beginning at the wide end of plug 14a or 14b) and then through diaphragm hole 38. The rubbery material of the diaphragm distorts to accommodate catheters of larger diameters, offering minimal resistance. The tip of catheter 34 is then passed through bore 32 of housing 12, and then, if desired, through diaphragm hole 38 and bore 15 of the second plug 14. Plugs 14a and/or 14b are then locked into housing 12 as described above. All other operations of this embodiment are as described above.

A further embodiment of the present invention is shown in the exploded perspective view of FIG. 10, in which the skin anchor is identical to that previously described, but the catheter grasping means is different. A rotatable core 40 is formed from an elastic material, and is elliptical rather than circular in cross section. Lever 42 is formed from a rigid material, and is a shaft that is disposed on and extends from a first end of rotatable core 40. This embodiment further includes a housing 44 which is eccentric in cross section, a bore 45, and a slit 48. A cross section through anchor track 20 is seen in FIG. 11 which shows anchors 16 in an unengaged position. FIG. 12 is the same cross section, showing anchors 16 in the engaged position.

FIG. 10 is a perspective view of rotatable core 40, showing a locking ridge 52 and lever 42. The end-on view of FIG. 14 demonstrates the elliptical cross section of rotatable core 40, as well as core slit 46 and a core bore 50 formed therein.

The longitudinal section through housing 44 seen in FIG. 15 shows locking groove 54. Referring to FIGS. 10–15, the separate parts seen in FIG. 10 are assembled (either at the factory before the anchoring device is packaged, or by the operator) by sliding core 40 into housing 44 so that locking ridge 52 engages locking groove 54.

A catheter 34 is passed lengthwise via slits 48 and 46 into core bore 50. Lever 42 is rotated clockwise, which in turn rotates core 40, such that the long axis of its eccentric cross section is compressed by the short axis of the eccentric cross section of housing 44. This in turn compresses core bore 50, which in turn causes increased friction with catheter 34, effectively securing it against longitudinal movement. The rotation of core 40 also brings slit 46 out of alignment with housing slit 48,so that catheter 34 cannot be stripped out lengthwise from core bore 50. The operation of anchors 16 is identical to that described for FIGS. 1–6.

Figure 16:
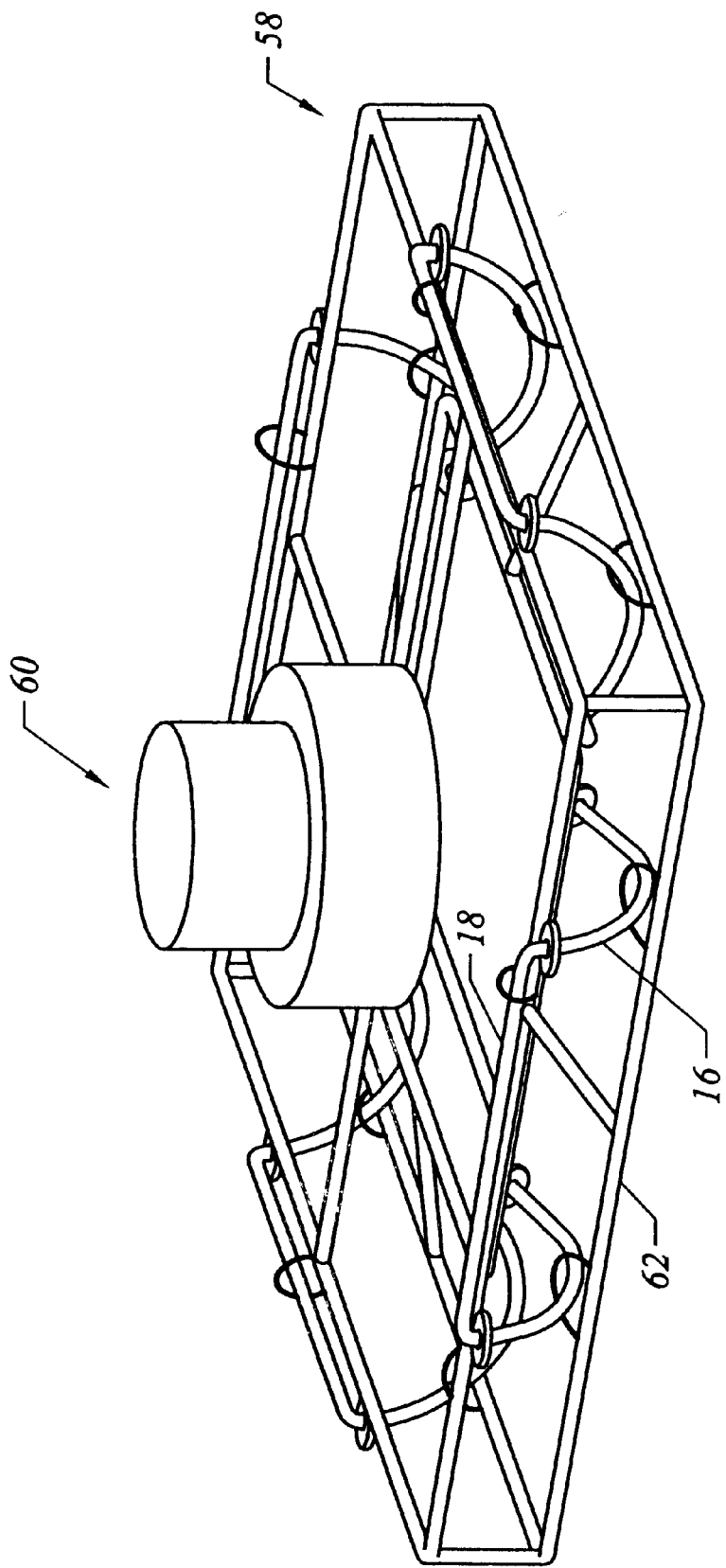
FIG. 16 is a perspective view of a universal base according to a fourth embodiment of the present invention.

FIG. 16 shows another embodiment according to the present invention. A universal base 58 is a lightweight platform for attachment of various apparatus to an inner or outer surface of the body (not shown). A universal post 60 is a cylinder formed from a rigid material, with a locking ridge (not shown), which protrudes from platform 62. Platform 62 is a wire grid designed to support universal post 60, as well as several anchors 16 (with attached anchor drive bars 18), here shown in the deployed position.

Universal base 58 is positioned by the operator over the desired portion of skin (or other tissue if being used internally). Anchors 16 are then driven into the skin or tissue by depressing anchor drive bars 18. The locking receptacle of the apparatus to be secured (not shown) is then pushed down onto post 60, locking it in place.

Figure 17:
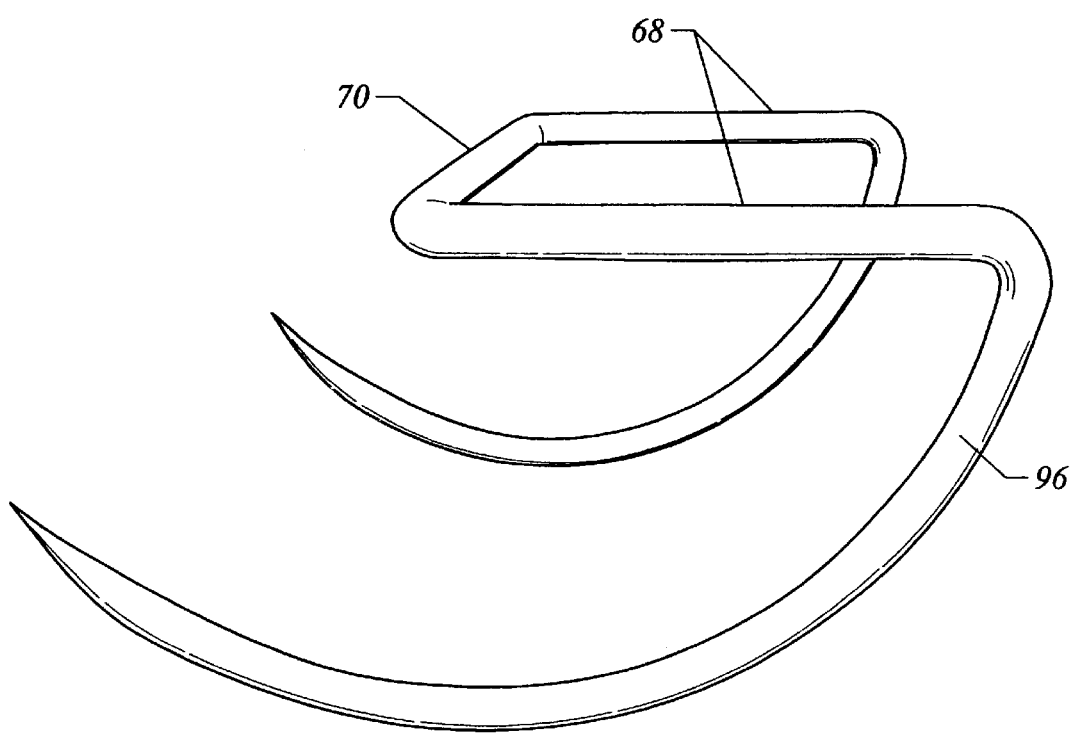
FIG. 17 is a radial anchor unit according to a fifth embodiment of the present invention.

FIGS. 17–21 show yet another embodiment according to the present invention. FIG. 17 shows a radial anchor unit consisting of two anchors 96 arranged in parallel. Anchors 96 are arcuate members that are sharpened at first ends thereof, and formed from any material suitable for use in medical applications, such as metal, plastic, or the like. A radius 68 projects from each of a second end of anchors 96 to the center of the circle defined by each anchor 96. A shaft 70 joins the ends of radii 68.

Figure 18:
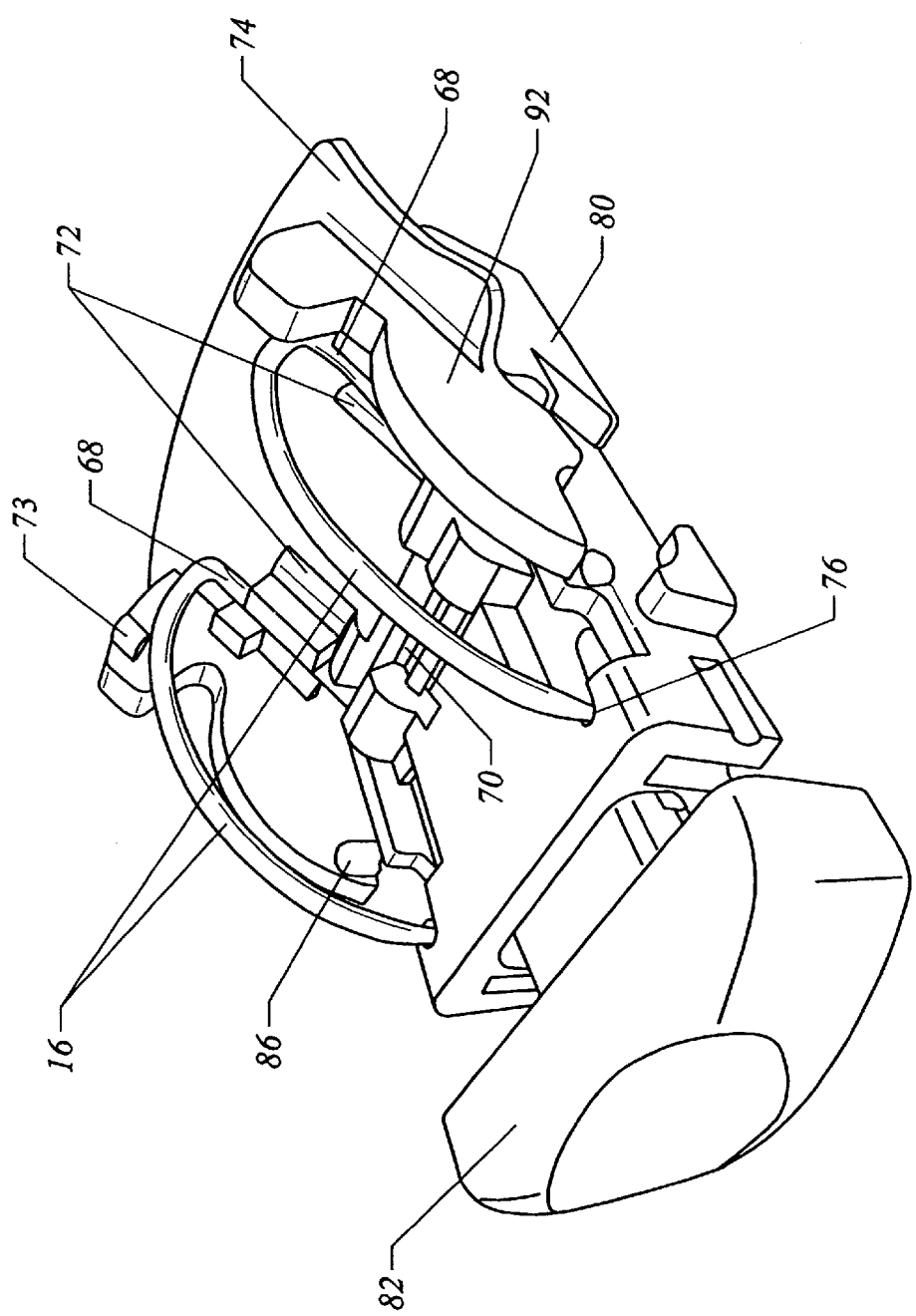
FIGS. 18 and 19 are perspective views of a radial anchoring device according to the fifth embodiment of the present invention, showing the device in the unengaged position.
Figure 19:
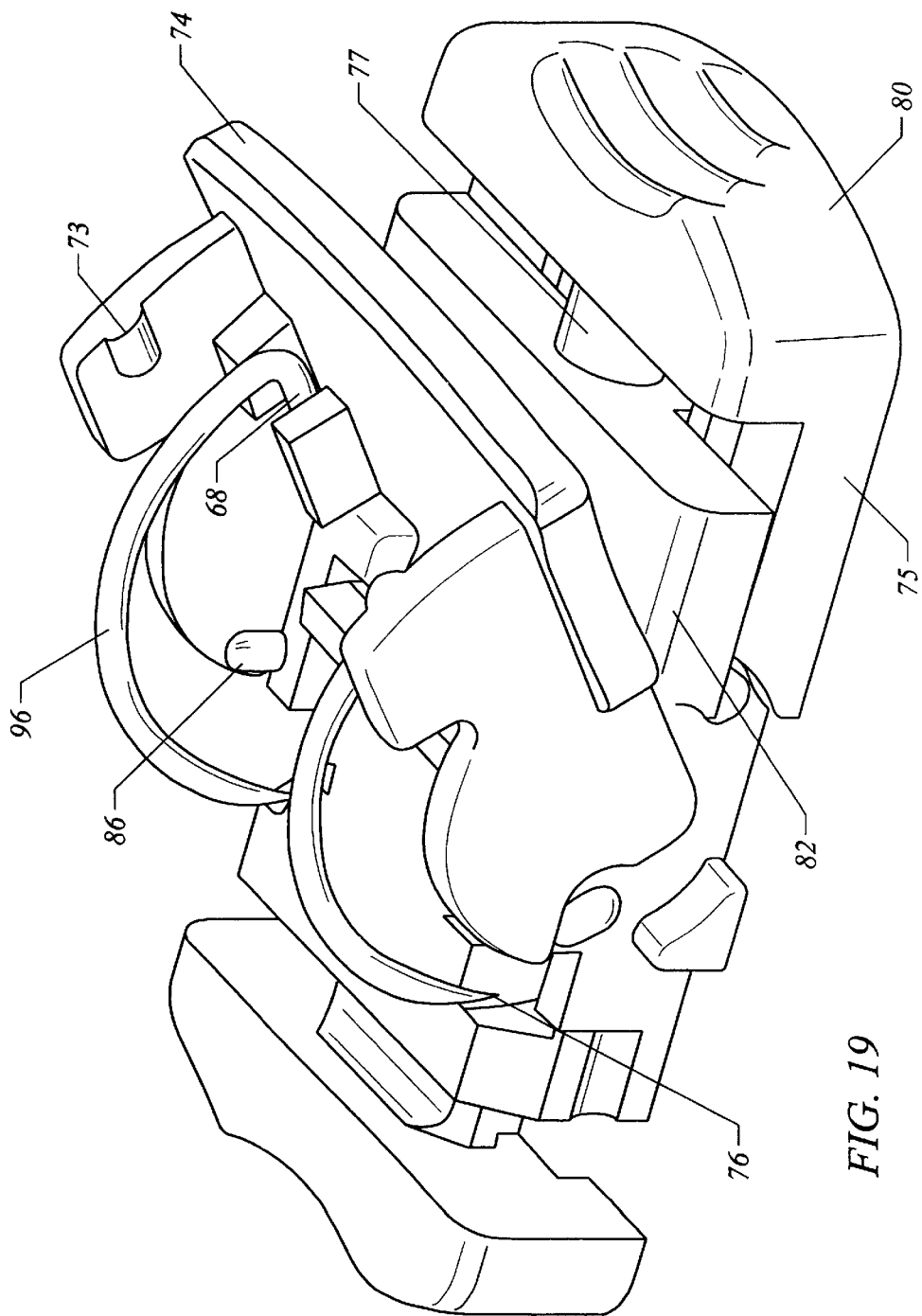
Figure 20:
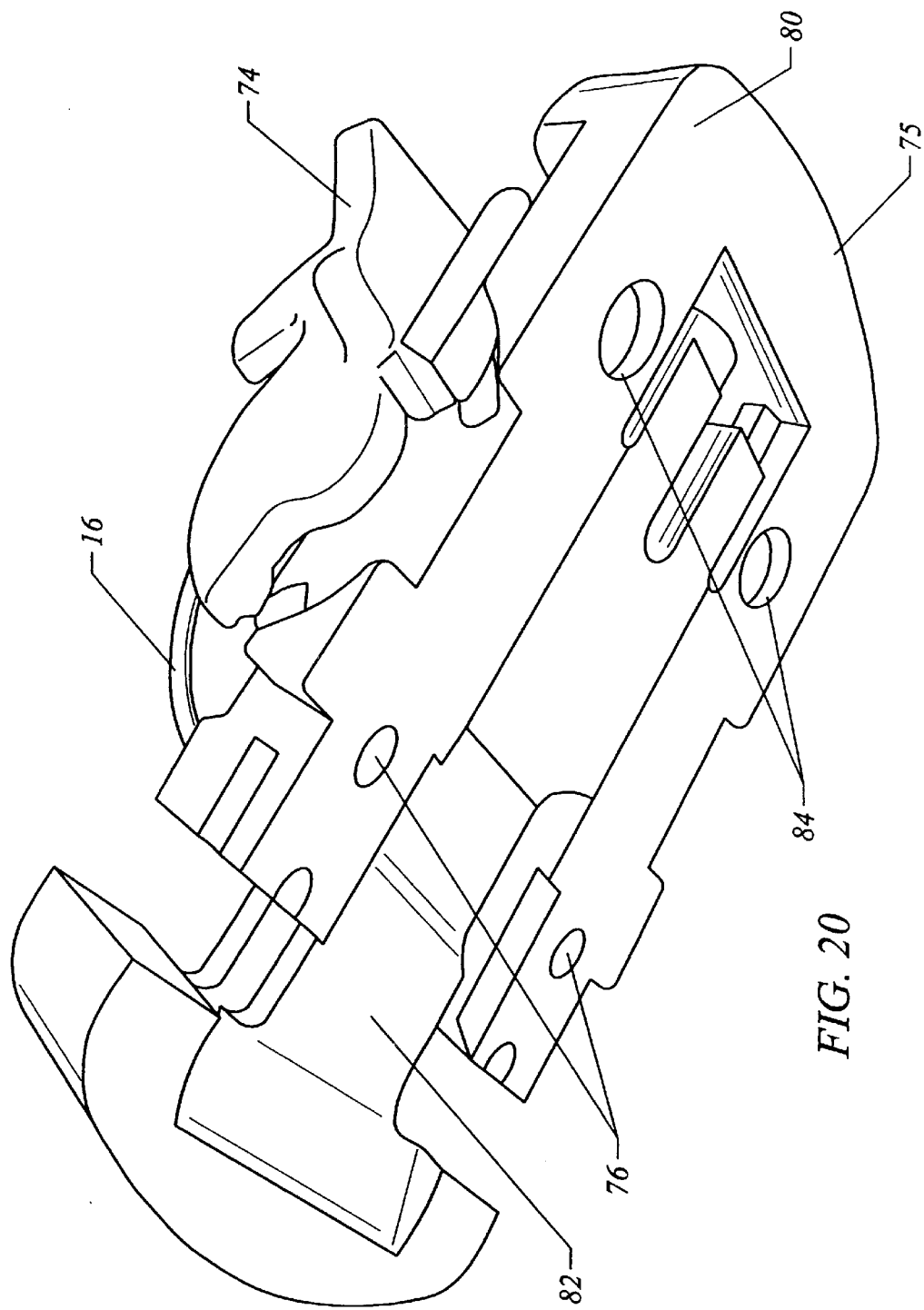
FIG. 20 is a bottom perspective view of the radial anchoring device shown in FIGS. 18 and 19, showing the device in the unengaged position.

FIGS. 18–20 show the radial anchoring device in the open position, before it has been deployed. FIG. 18 shows the anchor unit of FIG. 17 assembled into a housing 92. Axis 70 passes through two slots 72 on the housing 92, and radii 68 are each engaged in slots in anchor handle 74. The sharpened tips of anchors 96 are safely hidden within anchor bores 76. In FIG. 19, the side walls of anchor bores 76 are cut away, showing the sharpened tips of anchors 96. Spring 77 is also visible, disposed between primary jaw 80 and secondary jaw 82. Two anchor bores 76 are seen again in FIG. 20, which is a view of the base 75 of the device. Two anchor receptacles 84 are also seen. A groove can also be formed in the bottom surface of this device parallel to axis 70, which serves the same purpose as groove 22 shown in FIGS. 1–3 and described above. One of two engaged detents 73, and one of two lock-out detents 86, are visible in FIGS. 18 and 19.

Figure 21:
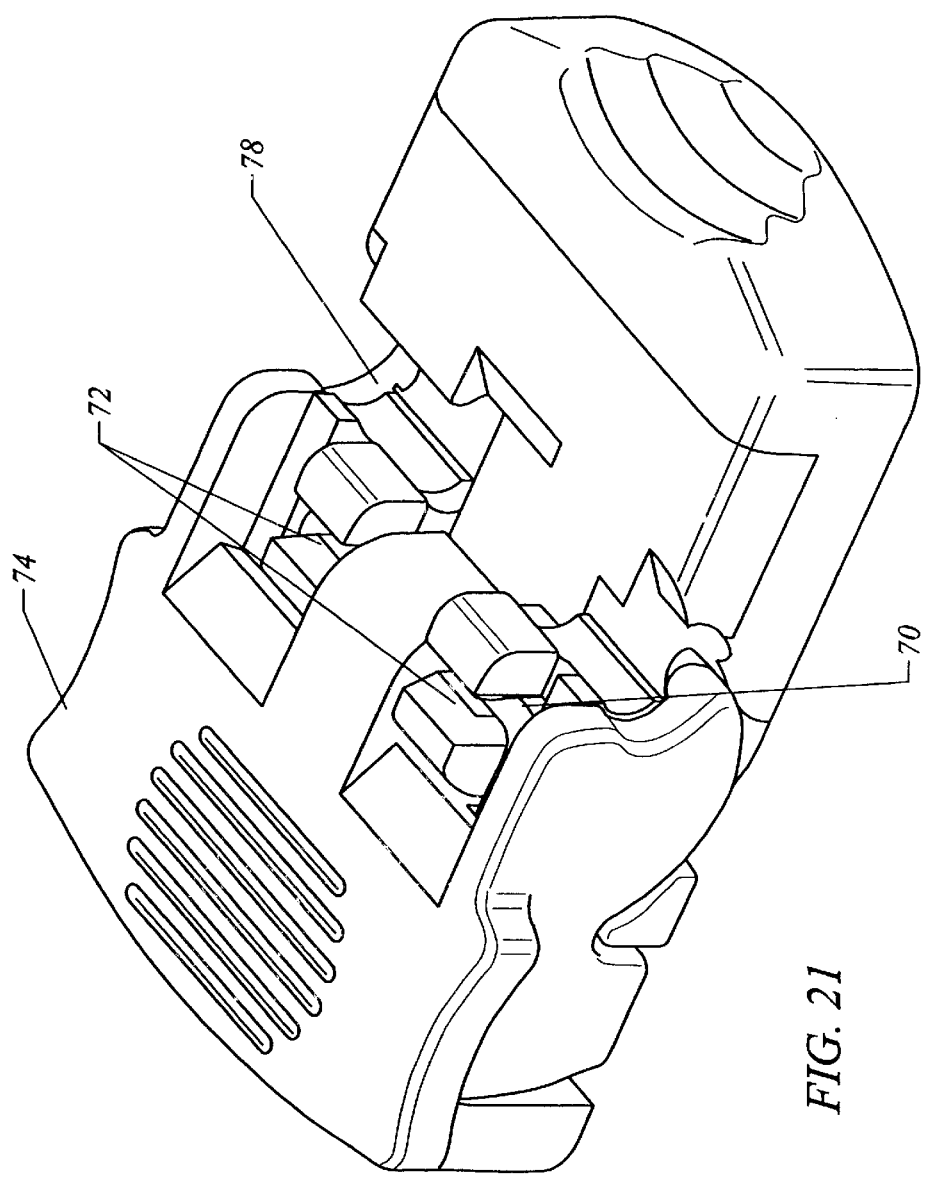
FIG. 21 is a perspective view of the radial anchoring device shown in FIGS. 18, 19, and 20, showing the device in the engaged position.

FIG. 21 shows the device in the closed position, after it has been deployed on the skin of a patient. A catheter channel 78 is shown running parallel to axis 70, only a small portion of which is visible between one of the slots 72 and the anchor handle 74.

The anchor unit shown in FIG. 17 is assembled into the housing 92 at the factory, in the open position depicted in FIGS. 18–20. The operator uses one hand to apply the unit to the patient so that base 75 is firmly pressed against the skin at the desired anchoring site. With the opposite hand, anchor handle 74 is rotated around axis 70. This applies pressure to radii 68, which, in turn, drive the sharpened points of anchors 96 down through anchor bores 76, then through the skin of the patient, and then back up into anchor receptacles 84. Detents on either side of anchor handle 74 click into depressions formed in housing 92, securing anchor handle 74 and anchors 16 in the engaged position shown in FIG. 21.

The catheter 34 is attached to the unit as follows. With the thumb and forefinger of one hand, the operator squeezes primary jaw 80 and secondary jaw 82 together by overcoming the biasing force of spring 77. This action widens the catheter channel 78 sufficiently so that the shaft of catheter 34 can be placed longitudinally into the channel 78 by the operator's opposite hand. The jaws 80 and 82 are then released and spring back into their original position, frictionally gripping catheter 34. This operation can be performed either before or after the device is secured to the skin as outlined in the paragraph above.

If for any reason the position of catheter 34 needs to be adjusted after it has been secured in the device, this is easily accomplished. The operator again squeezes primary jaw 80 and secondary jaw 82 together, freeing the catheter to move within catheter channel 78. With his/her opposite hand the operator slides catheter 34 to the desired new location, and then releases the jaws, again securing the catheter in place.

When the catheter and device are to be removed, the operator secures the base 75 against the skin with one hand, and with his/her opposite hand pulls the anchor handle 74 upward, overcoming the resistance of the detents 73 against the housing 12. The handle is rotated around axis 70 until lock-out detents 86 click into place against housing 92 (this occurs a few degrees of rotation past the original open position in which the unit is supplied from the factory). At this point the sharpened ends of anchors 96 are again safely hidden within anchor bores 76, preventing inadvertent needle-stick injury, and the unit can be safely disposed of. Note that this removal operation can be performed with the catheter 34 still engaged in the catheter channel 78.

Alternatively, the catheter 34 can be removed from catheter channel 78 by reversing the procedure described above for its placement.

In each of the embodiments described above, the apparatus-securing devices provide a simple, inexpensive, self-contained device for securing any portion of the length of a catheter to a patient's skin without the risk of needle-stick injuries (with their attendant risks of HIV, hepatitis C and other infectious diseases). The sharp points of the anchors are never exposed except at the instant that they are traversing the skin or tissue of the patient during application or removal. At all other times (i.e. before use, and upon conclusion of application or removal) the sharp points of the anchors are safely hidden within the housing, either in the anchor track or the anchor recess, and they are secured in those positions by the engagement of the anchor drive bar or anchor handle with the housing.

Application, removal, or repositioning of the catheter can each be accomplished in an instant. The catheter can be securely anchored, even in adverse circumstances in which other techniques are inadequate. For example, adhesives are not reliable in the very sweaty patient, but the device described works equally well with wet or dry skin. Similarly, suturing is very difficult and dangerous when the patient is uncooperative and only able to hold still for a moment at a time, but the invention described here can be applied during that instant, without risk to patient or operator.

There exist other suitable embodiments of the invention than what has been previously described. For example, the device of FIGS. 1–9 can be furnished with one plug rather than two. The cross section of the plugs depicted in FIGS. 1–6 need not be round; it can be square, oval, or any other shape. Similarly a variety of cross-sectional shapes can be used for the core and housing depicted in FIGS. 10–15. The plug depicted in FIGS. 7–9 can have a narrow slit, allowing the catheter to be loaded lengthwise, rather than tip first.

The bore depicted in any of the figures can be placed off-center. Specifically, in the plugs depicted in FIGS. 1–9, the bore can be positioned closer to the base of the device, so that the catheter does not travel as great a vertical distance to enter the skin. The same result can be accomplished for the device shown in FIGS. 10–15 by placing the housing slit on the side instead of on top of the device, and moving the bore in the core member away from the central axis and closer to the slit edge. In this way a 90-degree rotation of the core will simultaneously compress the bore and bring it closer to the skin surface.

The device can be furnished with only one of the arcuate anchors of the sort described above, or with three or more such anchors, each rotating around an axis parallel to that of the catheter. Such arcuate anchors can be provided on either side of the device, rotating in opposite directions. Alternatively, the anchors can be disposed on either side of the device, but rotate around an axis perpendicular to that of the catheter. The cross section of these anchors can be round, as depicted, or it can have any of a variety of other shapes. For example, a "V" or "C" shape can be used to provide greater rigidity or to provide a conduit for body fluid to escape as the anchor pierces tissue. The pathway for these anchors can be defined by two or more tabs protruding from the housing, each with a hole in it to serve as a guide for the anchor. In this fashion the manufacturing process can be simplified as the need for curved anchor tracks is eliminated.

Alternatively, the anchors need not be curved at all. For example, straight anchors can be placed in the housing, in a plane parallel to that of the skin, with their points aimed at the skin groove. After the housing has been pressed onto the skin, the points of the straight anchors can be pushed through the ridge of skin which has been pushed up into the groove and then into anchor tracks on the opposite side of the housing. A single straight anchor can be used, or several can be arranged in parallel, with a single drive bar to push them all at once. Any of the anchors described can be driven by a spring, loaded in the unengaged position, rather than finger pressure from the operator.

Figure 24:
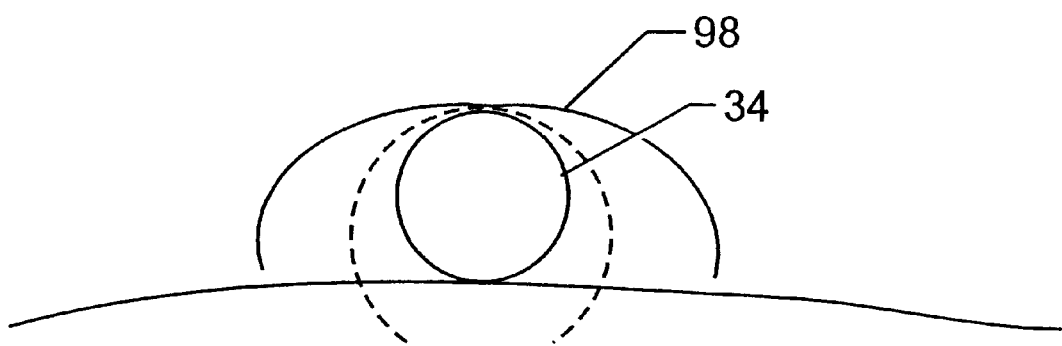
FIG. 24 is an axial view of a further alternative embodiment of the present invention showing a deformable anchor for holding a device in position.

Other anchors are suitable in the practice of the invention. For example, a conventional deforming surgical staple can be employed along with a simple staple driver, which can be detachable after it has been used. Alternatively, as shown in FIG. 24, a staple 98 of a resilient material can be deployed in an open, deformed position on the device 34, such that when released (shown in phantom in FIG. 24), it springs back into its closed, non-deformed position, and in so doing its points engage the skin. This sort of anchor can be furnished with a mechanism for re-opening the staple at such time as it needs to be unengaged. A single helical coil of resilient material can serve both as anchor and as means for grasping the catheter-in its open, deformed position the catheter could pass freely through the center of the coil. When released the coil will spring back into its non-deformed, more tightly wound shape, and in so doing drive its pointed ends into the skin while simultaneously gripping the catheter at its center more tightly.

Figure 22:
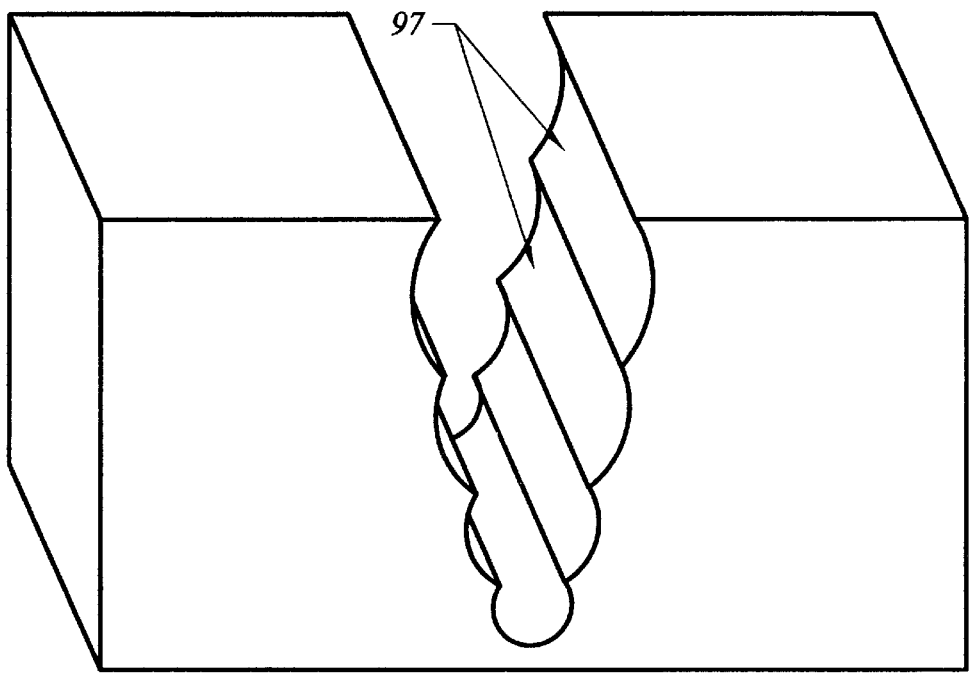
FIG. 22 is a perspective view of a device-grasping means according to a sixth embodiment of the present invention.
Figure 23:
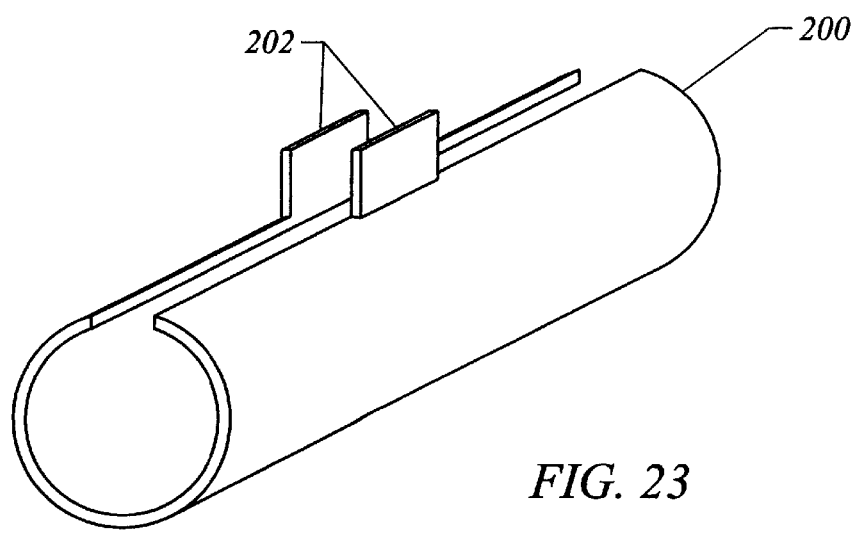
FIG. 23 is a view of a further embodiment of the present invention showing tabs for facilitating opening of the device.

Many alternative means can be employed for grasping the catheter. For example, the core and housing described in FIGS. 10 and 13–15 can have any of a variety of eccentric (non-circular) cross sections: elliptical or polyhedral, with or without ridges or teeth provided on opposing surfaces for additional friction. An entirely different grasping means consists of a cylinder 200 of a resilient material as shown in FIG. 23, with a slit cut along its length and with tabs 202 provided on either side of the slit can be used. Pressure from the operator's thumb and forefinger against these tabs opens the cylinder, releasing the catheter. Or such a cylinder can be provided with a hinge along one of its sides, and a slit along the opposite, with a latching mechanism so that the slit can be fastened in a closed position after the catheter had been adjusted to the desired location. Another approach is to use an open channel of a rubbery material, the bore of which is slightly smaller than that of the catheter, so that pressing the catheter into the channel compresses it slightly and results in a frictional grip. Referring to FIG. 22, a stack of such channels 97 (e.g., in V-shape configuration) of varying diameters, with the largest outermost and the smallest innermost, can be provided so that a variety of catheters can be accommodated. Any combination of anchor and catheter-grasping means can be used.

The base of the device, which comes in contact with the patient's skin, can be provided with a pad of cushioning material for increased comfort. Such a pad can also contain antiseptic material to decrease the possibility of wound infection, or coagulant materials such as topical thrombin or microfibrillary collagen to prevent bleeding in patients with a bleeding disorder. The base may also be furnished with channels leading from the anchors to the periphery of the device, allowing for the egress of any exudate from the anchor wounds, and allowing for the ingress of antibiotic ointment to those wounds.

Moreover, the application of this attachment device is not limited to securing vascular catheters, or indeed to catheters at all. It is equally applicable to securing a variety of apparatus such as chest tubes (thoracostomy tubes), pacemakers, insulin or other drug pumps, glucose monitors, transcutaneous electrical nerve stimulation (TENS) units, surgical drains, surgical mesh, etc.—to either an outer or inner surface of the body.

The preceding description of the invention has been presented for the purposes of illustration and description. It is not intended to be exhaustive or to limit the invention to the precise form disclosed. Many modifications and variations are possible in light of the above teachings. It is intended that the scope of the invention be limited not by this detailed description, but rather by the claims appended hereto.

What is claimed is:

1. An apparatus for anchoring a device to tissue of an individual, comprising:
   (a) a device-grasping means for holding a device, and
   (b) an anchoring means for anchoring said device-grasping means to a patient's tissue, wherein said anchoring means includes at least two anchors that are arcuate in shape, and a first end of each of said at least two anchors has a sharpened point, wherein said at least two anchors are disposed parallel to each other, and a structural connector is connected to and extends between said at least two anchors.

2. The apparatus of claim 1, wherein said anchoring means may be reversibly deployed between a first unengaged position and a second engaged position.

3. The apparatus of claim 2, wherein said anchoring means is biased toward said second engaged position by means of a biasing means.

4. The apparatus of claim 1, wherein said anchoring means includes at least one recess in which said first ends of said at least two anchors can be deployed.

5. The apparatus of claim 4, wherein said anchoring means includes a first and a second recess, wherein said first ends of said at least two anchors are deployed in said first recess when in a first unengaged position and deployed in said second recess when in a second engaged position.

6. The apparatus of claim 1, wherein said device-grasping means further comprises:
   (a) a housing, said housing having a first bore extending therethrough, and;
   (b) at least one plug, said at least one plug formed from an elastic material and having a second bore that extends therethrough, said at least one plug shaped to securely fit into either end of said first bore in said housing.

7. The apparatus of claim 6, wherein a slit extends from an outer circumference of said at least one plug to said second bore.

8. The apparatus of claim 6, said housing including a groove in a portion of said housing for receiving said patient's tissue.

9. The apparatus of claim 6, wherein
   (a) said at least one plug includes a ridge that extends around an outer circumference thereof, and
   (b) said housing includes a groove that extends around an inner circumference of said first bore, whereby said ridge will engage said groove at a point at which said at least one plug is properly engaged with said housing.

10. The apparatus of claim 6, wherein said at least one plug includes a flange that extends around an outer circumference of a first end thereof.

11. The apparatus of claim 6, wherein said at least one plug is attached to said housing by means of a hinge.

12. The apparatus of claim 11, wherein said device-grasping means is tubular in shape and is formed from a resilient material, and further includes a slit that is formed in and extends along the length of said device-grasping means.

13. The apparatus of claim 12, wherein at least one tab is disposed on said device-grasping means on each side of said slit, whereby said tabs can be used to deform said device-grasping means such that a diameter thereof is temporarily increased.

14. The apparatus of claim 1, wherein said device comprises at least one catheter.

15. The apparatus of claim 14, wherein said device-grasping means holds said at least one catheter in a position generally parallel to said patient's tissue.

16. An apparatus for anchoring a device to tissue of an individual, comprising:
    (a) a device-grasping means for holding a device, said device-grasping means including:
       (i) a housing, said housing having a first bore extending therethrough, and;
       (ii) at least one plug, said at least one plug formed from an elastic material and having a second bore that extends therethrough, said at least one plug shaped to securely fit into either end of said first bore in said housing; and
    (b) an anchoring means for anchoring said device-grasping means to a patient's tissue, wherein said anchoring means includes a housing and at least two anchors, and a first end of each of said at least two anchors has a sharpened point, said housing including a first lip and a second lip, said first lip capable of securing said anchoring means in a first unengaged position, and said second lip capable of securing said anchoring means in a second engaged position.

17. An apparatus for anchoring a device to tissue of an individual, comprising:
    (a) a device-grasping means for holding a device, and
    (b) an anchoring means for anchoring said device-grasping means to a patient's tissue, said anchoring means including:
       at least two anchors, a first end of each of said at least two anchors having a sharpened point,
       a housing, said housing having a first bore extending therethrough, and
       at least one plug, said at least one plug formed from an elastic material and having a second bore that extends therethrough, said at least one plug shaped to securely fit into an end of said first bore in said housing, wherein said second bore extending through said at least one plug includes a first opening and a second opening, said first opening smaller than said second opening, and said at least one plug further includes a diaphragm formed of an elastic material that extends around an inner circumference of said first opening.

18. An apparatus for anchoring a device to tissue of an individual, comprising:
    (a) a device-grasping mechanism for holding a device,
    (b) an anchoring mechanism for anchoring said device-grasping mechanism to a patient's tissue, said anchoring mechanism including:
       at least two anchors, a first end of each of said at least two anchors having a sharpened point,
       a housing, said housing having a first bore extending therethrough, and an inner core formed from an elastic material and capable of holding said device, said inner core capable of being supported in a fixed position within said housing;

wherein a first end of said inner core includes a lever attached thereto, and a second end of said inner core includes a ridge that extends around said outer circumference;

wherein said inner core can be secured in said housing by engaging said ridge and said groove, and rotating said inner core by means of said lever.

19. An apparatus for anchoring a device to tissue of an individual, comprising:

(a) a device-grasping means for holding a device, and (b) at least two anchors for anchoring said device-grasping means to a patient's tissue, wherein said at least two anchors are arcuate in shape, parallel to each other and a first end of each of said at least two anchors has a sharpened point, said at least two anchors further include:

at least two members, each of said at least two members extending from each second end of said at least two anchors toward a center of a circle defined by each of said at least two anchors, and;

a shaft, said shaft connected to and extending between said at least two members.

20. The apparatus of claim 19, wherein said anchoring means further comprises an anchor handle attached to said at least two anchors, and said anchoring means is rotatably fixed to said device-grasping means and rotates between a first unengaged position and a second engaged position around a central axis defined by said shaft.

21. The apparatus of claim 19, wherein said device-grasping means further comprises a first jaw and a second jaw, wherein said device is held in place between said first jaw and said second Jaw.

22. The apparatus of claim 21, wherein said device is held in place between said first jaw and said second jaw by means of a biasing means.

23. An apparatus for anchoring a device to the body of an individual, comprising:

(a) a device-grasping means for holding a device, and (b) an anchoring means for anchoring said device-grasping means to a patient's tissue, said anchoring means comprising at least one anchor formed from a deformable material, said anchor having a first position in which said anchor is deformed, open, and unengaged and a second position in which said anchor is non-deformed, closed, and engaged, wherein when said anchor is deployed in said first position and is released it automatically moves to said second position and engages with said patient's tissue.

24. An apparatus for anchoring a device to tissue of an individual, comprising:

(a) a device-grasping mechanism for holding a device, and (b) an anchoring mechanism for anchoring said device-grasping mechanism to a patient's tissue, wherein said anchoring mechanism includes at least two anchors, and a first end of each of said at least two anchors has a sharpened point, wherein said at least two anchors are disposed parallel to each other, and a shaft is connected to and extends between said at least two anchors.

* * * * *

UNITED STATES PATENT AND TRADEMARK OFFICE
CERTIFICATE OF CORRECTION

PATENT NO. : 6,572,587 B2
DATED : June 3, 2003
INVENTOR(S) : Lerman

It is certified that error appears in the above-identified patent and that said Letters Patent is hereby corrected as shown below:

Column 13,
Line 66, after "claim" delete "11" and substitute -- 1 --.

Signed and Sealed this

Twenty-fifth Day of January, 2005

JON W. DUDAS
*Director of the United States Patent and Trademark Office*